United States Patent [19]

Heinrich

[11] Patent Number: 5,082,774
[45] Date of Patent: Jan. 21, 1992

[54] RECOMBINANT HUMAN NERVE GROWTH FACTOR

[75] Inventor: Gerhard Heinrich, Acton, Mass.

[73] Assignee: The General Hospital Corporation, Boston, Mass.

[21] Appl. No.: 238,368

[22] Filed: Aug. 30, 1988

[51] Int. Cl.$^5$ .................. C12N 21/06; C12N 15/00; C12N 5/00

[52] U.S. Cl. ................. 435/69.1; 435/172.3; 435/240.2; 435/320.1; 935/11; 935/22; 935/70

[58] Field of Search ............. 435/68, 240.2, 320, 435/320.1, 240.2, 172.3, 317.1, 69.1; 530/350, 397; 935/11, 70, 111

[56] References Cited

U.S. PATENT DOCUMENTS

| | | | |
|---|---|---|---|
| 4,675,285 | 6/1987 | Clark et al. | 435/6 |
| 4,740,461 | 4/1988 | Kaufman | 435/68 |
| 4,770,999 | 9/1988 | Kaufman et al. | 435/68 |
| 4,810,643 | 3/1989 | Souza | 435/68 |

FOREIGN PATENT DOCUMENTS 0121338 3/1984 European Pat. Off.
WO/8800975 2/1977 PCT Int'l Appl.

OTHER PUBLICATIONS

Edwards, "Differential RNA Splicing Predicts Two Distinct Nerve Growth Factor Precursor", *Nature*, 319:784 (Feb. 27, 1986).

Hallbook, et al., "Production and Characterization of Biologically Active Recombinant Beta Nerve Growth Factor," *Molecular and Cellular Biology*, Jan. 1988, pp. 452-456.

Ullrich, et al., "Human B-Nerve Growth Factor Gene Sequence Highly Homologous to that of Mouse," *Nature*, 303:821-825, Jun. 1983.

Kaufman, et al., "Amplification and Expression of Sequences Cotransfected with a Modular Dihydrofolate Reductase Complementary DNA Gene," *J. Mol. Biol.* (1982) 159:601-621.

Lusky, et al., "Characterization of the Bovine Papilloma Virus Plasmid Maintenance Sequences," *Cell*, Jan. 1984, 36:391-402.

Kaufman, "Identification of the Components Necessary for Adenovirus Translational Control and their Utilization in cDNA Expression Vectors," *Proc. Natl. Acad. Sci. USA*, 82:689-693, Feb. 1985.

Primary Examiner—Elizabeth C. Weimar
Assistant Examiner—Jasemine C. Chambers
Attorney, Agent, or Firm—Fish & Richardson

[57] ABSTRACT

An expression vector replicable in a mammalian cell includes a prepro-NGF encoding DNA sequence operably linked with regulatory DNA capable of effecting the expression of the prepro-NGF encoding DNA sequence in the cell. Also, a mammalian cell is transfected with such an expression vector. Also, a method for making recombinant human nerve growth factor includes transfecting a mammalian cell with such an expression vector, maintaining the cell in a culture medium, and isolating recombinant human nerve growth factor from the medium. Also, a composition includes recombinant human nerve growth factor made according to such a method combined with a pharmaceutically acceptable carrier.

9 Claims, 1 Drawing Sheet

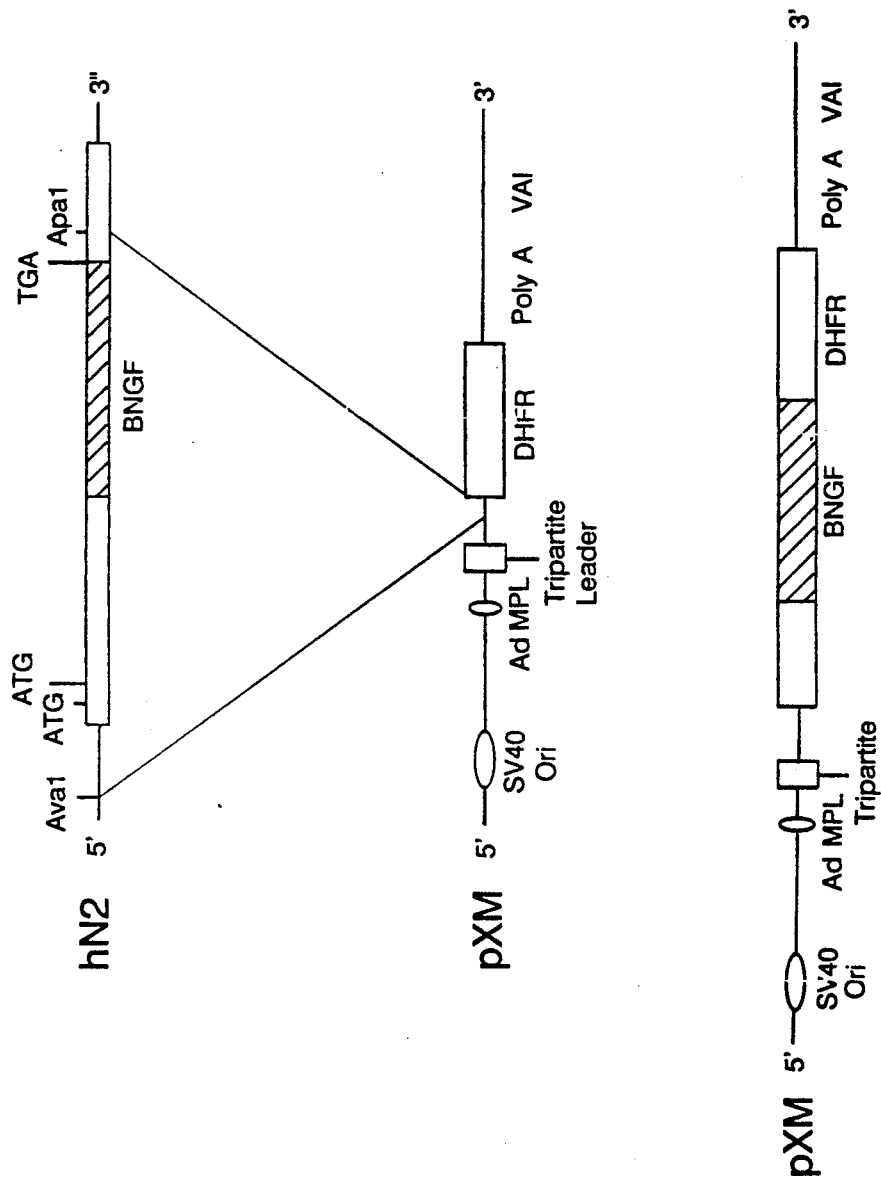
FIGURE

RECOMBINANT HUMAN NERVE GROWTH FACTOR

BACKGROUND OF THE INVENTION

This invention relates to human nerve growth factor.

Nerve growth factor ("NGF") is a polypeptide that is important for the differentiation and survival of sympathetic, sensory, and central cholinergic neurons. Studies in non-human animals have suggested that NGF may be beneficial for the treatment of human diseases, including Alzheimer's and other degenerative diseases, stroke, peripheral nerve injuries and neuropathies, and for post surgical support. Human NGF ("hNGF") is a rare polypeptide in human tissues, and derivation of hNGF from human tissues cannot provide amounts sufficient to supply the potential therapeutic and research needs.

Mature NGFs are known to be derived from prepro-NGFs by proteolytic cleavage. At the 3' end of the NGF gene from rat, chicken, bovine, and human is a large exon ("exon 4") which encodes 243 amino acids of the prepro NGF. Three additional short 5' exons are known in the mouse NGF gene. F. Hallböök et al., Mol. Cell. Biol., Vol. 8, pp. 452-56 (1988), describes using a mammalian expression vector system for synthesis, from fragments of the rat NGF gene or from the chicken NGF gene, of a recombinant NGF that is similar to NGF purified from mouse submandibular gland. The chicken NGF construct of Hallböök et al. includes the 3' exon of the chicken NGF gene, and their rat NGF construct includes a 771-bp fragment from the 3' exon of the rat NGF gene.

European Patent Publication No. 0 121 338 describes expressing human β-NGF in *E. coli* as a mature polypeptide, using a mature NGF-encoding fragment of the human NGF gene.

SUMMARY OF THE INVENTION

In general, in one aspect, the invention features an expression vector replicable in a mammalian cell, the vector comprising a prepro-NGF encoding DNA sequence operably linked with regulatory DNA capable of effecting the expression of the prepro NGF encoding DNA sequence in the mammalian cell. A DNA sequence encoding prepro NGF, as that term is used herein, refers to a DNA sequence which encodes the mature NGF protein and, in addition, an amino acid chain 5' to (i.e., upstream of) the mature protein. In a propro-protein generally, the amino acid chain upstream of a mature protein includes a "propeptide", adjacent the mature protein, and a "prepeptide" adjacent the propeptide. The propeptide is normally cleaved inside the cell after expression, adn the prepeptide is subsequently normally cleaved during secretion.

In preferred embodiments the prepro-NGF encoding DNA sequence consists essentially of the coding region of exon 4 of the human NGF gene; and the expression vector is plasmid VP2.

In another aspect the invention features a mammalian cell transfected with an expression vector replicable in the cell, the vector comprising a prepro NGF encoding DNA sequence operably linked with regulatory DNA capable of effecting the expression of the prepro-NGF encoding DNA sequence in the cell; the cell is transiently or is stably transfected with the expression vector.

In preferred embodiments the cell is a COS cell or a CHO cell.

In another aspect the invention features a method for making recombinant human nerve growth factor, comprising transfecting a mammalian cell with an expression vector replicable in the cell, the vector comprising a prepro NGF encoding DNA sequence operably linked with regulatory DNA capable of effecting the expression of the prepro-NGF encoding DNA sequence in the cell, maintaining the mammalian cell in a culture medium, and isolating recombinant human nerve growth factor from the medium.

In another aspect the invention features a composition including recombinant human nerve growth factor made according to the method of the invention combined with a pharmaceutically acceptable carrier.

We have discovered that the 3' exon ("exon 4") of the hNGF gene contains the necessary genetic information to yield biologically active hNGF when expressed in mammalian cells. Moreover, the precursor is processed correctly, so that the recombinant hNGF is secreted into the culture medium. The invention makes possible the large scale production of rhNGF in quantities sufficient for therapeutic uses, such as, for example, treatment of Alzheimer's disease, as well as for further research.

Other features and advantages of the invention will be apparent from the following description of the preferred ambodiments thereof, and from the claims. dr

DESCRIPTION OF THE PREFERRED EMBODIMENTS

The FIGURE is a diagram showing the construction of an expression vector according to the invention.

Abbreviations used in the FIGURE and in the description are as follows: NGF, βNGF, β subunit nerve growth factor; hNGF, human NGF; rhNGF, recombinant human NGF; EIA, enzyme immunoassay; BSA, bovine serum albumin; SV40 Ori, SV40 origin of replication; AdMLP, adenovirus major late promoter; DHFR, dihydrofolate reductase.

Construction

Generally, an expression vector according to the invention includes the coding regions of the hNGF gene exon 4. In a mammalian host cell the hNGF gene fragment is transcribed into an mRNA for prepro-hNGF, which is in turn translated into a prepro hNGF. The prepro hNGF is then processed, or cleaved, to form mature hNGF, which is secreted into the medium of the host cell.

Cloning of the Human NGF Gene

A 2.5 kb fragment of the mouse NGF gene containing the 3' exon (the exon which encodes mouse NGF) was $^{32}$P labeled and used to screen a human genomic library provided by Tom Maniatis, Harvard Biological Laboratories, Cambridge, Mass. Several recombinant bacteriophages containing the corresponding 3' exon, referred to here as exon 4, of the human NGF gene were obtained. A BqlII fragment from one of these was subcloned into the BamHl site of the plasmid pGEM3. Restriction enzyme analyses and blot hybridization, and comparison of the resulting data with the sequence of the human NGF gene, described in A. Ullrich et al., Nature, Vol. 303, pp. 821-25 (1983) (hereby incorporated by reference), show that the recombinant plasmid, named hN2, contains a portion of intron 3, all of exon 4, and a portion of the 3' flanking region of the human NGF gene.

Construction of the Expression Vector

The vector according to the invention includes exon 4 of the hNGF gene linked downstream from another exon. Fusion occurs within introns, and thus construction of the vector entails splicing a foreign exon to hNGF exon 4 to form a "minigene" having two heterologous exons. In the vector described here the 3' end of the hNGF gene is replaced with the coding region and the 3' end of the dihydrofolate reductase ("DHFR") gene.

Plasmid hN2, described above, was transfected into the dam⁻ strain of *E. coli* GM121. Unmethylated plasmid hN2 DNA was cut with AvaI and ApaI. The 969 bp AvaI/ApaI fragment, containing exon 4 of the hNGF gene, was blunt-ended with Klenow enzyme and purified by agarose gel electrophoresis. A derivative of a recombinant plasmid pXM that contains the mouse GM-CSF cDNA (pXMT2 musCSF) was obtained from Genetics Institute, Cambridge, Mass. The plasmid was cut with PstI, blunt-ended with T4 DNA polymerase, and the large fragment was purified by agarose gel electrophoresis. This fragment contains all sequences of pXMT2-musCSF except the cDNA insert. The gel-isolated and blunt-ended AvaI/ApaI fragment of hN2 was ligated into the large blunt-ended pXMT2-musCSF fragment, and transfected into *E. coli* C600. The orientation of the hNGF gene fragment was determined by restriction enzyme digestions and blot hybridizations, using as a probe a synthetic oligonucleotide that is complementary to 30 bases of exon 4 of the NGF gene. Recombinants in which Ad MLP and NGF sequences were in the same orientation were named VP2. These steps and the overall structure of VP2 are outlined in FIGURE 1.

The recombinant plasmid VP2 contains the strong major late promoter derived from the adenovirus genome ("Ad MLP"). This is followed by a mini exon, also from the adenovirus ("ADV") genome, the tripartite leader, and a very short intron. The ADV and hNGF gene fragments are fused in this intron and within intron 3 of the hNGF gene 150 bp upstream from the 5' end of exon 4. At the 3' end the hNGF gene fragment is joined at the ApaI site in the 3' untranslated region to the 5' untranslated region of the DHFR cDNA. The ADV/hNGF/DHFR fusion mRNA resulting from transcription of this minigene is expected to be approximately 2 kb in length.

Other conventional mammalian expression vectors can be used in place of pXM. For example, p91023(B), which is functionally similar in many respects to pXM, can be used. The construction of p91023(B) and its use as an expression vector are described in U.S. Pat. No. 4,675,285, particularly with reference to FIG. 3 therein. Expression vector p91023(B) is available from the ATCC undder accession number ATCC 39754, containing a human GM-CSF cDNA insert in the EcoRI cloning site of the vector. The human GM-CSF cDNA can be conveniently excised from p91023(B) using EcoRI, and the gel-isolated AvaI/ApaI fragment of hN2 can then be ligated into the vector DNA at that site, for example with appropriate linkers. The resulting p91023(B)-NGF expression vector can then be used as described above for the VP2 vector.

Expression of VP2

VP2 DNA was expressed in COS cells. For expression, COS cells were grown to confluency in DMEM supplemented with 10% fetal calf serum ("FCS"), subcultured, and transfected with 10 μg plasmid DNA/dish at ⅔ confluency using the DEAE dextran method, generally as described in M. Lopata et al., Nucleic Acid Res., Vol. 12, pp. 5707–17 (1984). Cells were grown for another 2 days in complete medium, and then for 1 day in serum free medium. The medium was collected and assayed for NGF by EIA. In an alternative bioassay, transfected cells were grown for three days in complete medium, and the medium was then collected, and diluted 1:3 with DMEM containing 5% horse/10% fetal calf serum. PC 12 cells were then grown in the diluted COS cell conditioned medium.

Analysis of VP2-Transfected COS Cells for VP2 mRNA

Total RNA was extracted from COS cells, and COS cells transfected with VP2 or a control plasmid, by the guanidine thiocyanate and cesium chloride centrifugation method, generally as described in V. Glisin et al., Biochemistry, Vol. 13, pp. 2633–36 (1974). 10 μg of total RNA were assayed for mRNAs containing hNGF gene sequences by Northern blot hybridization. RNA was treated with formaldehyde, electrophoresed through a 1.5% agarose gel containing 6% formaldehyde, and transferred to nylon membranes. The membranes were hybridized with BqlII/ApaI fragment of hN2. The DNA was labeled with $^{32}P$ to a specific activity of $10^8$ cpm/μg by priming DNA synthesis with random sequence oligonucleotide hexamers. Blots were hybridized in 50% formamide and 1M NaCl at 60° C. and washed at 60° C. in 0.15M NaCl.

Northern blot analyses showed that RNA extracted from COS cells transfected with VP2, and not RNA extracted from COS cells transfected with a control plasmid, contains an RNA of approximately 2 kb that hybridizes to hNGF gene sequences. These results are consistent with efficient transfection of COS cells with VP2 and active transcription into an RNA containing hNGF sequences. The 2 kb RNA probably represents the expected chimeric mRNA, resulting from transcription initiated at the Ad MLP.

Enzyme Immunoassay of Crude and Fractionated Culture Media

For measurements of hNGF, a commercially available EIA system was used, containing a monoclonal antibody (clone 27/21) against mouse 2.5S β-NGF, a conjugate of β-galactosidase with the same antibody, the enzyme substrate o-nitrophenol-β-D-galactopyranoside, and the proteinase inhibitor aprotinin (Boehringer-Mannheim, Indianapolis, Ind.). Clone 27/21 monoclonal antibody recognizes with high affinity a single epitope that is exposed in the NGF dimer. 2.5 S mouse submaxillary gland NGF (Collaborative Research, Waltham, Mass.) was used as standard. The EIA was carried out in Nunc (Denmark) immunoplates as recommended by the supplier. The concentration of Mab was 0.3 μg/ml. The β-galactosidase conjugate was 10 mu/well, and substrate was 1 mg/ml. Crude medium was diluted at least 1:50, and fractionated medium samples 1:1 with sample buffer for the assay. All samples were assayed in triplicates.

The EIA detected immunoreactive material only in medium conditioned by VP2-transfected COS cells, and not in medium conditioned by COS cells transfected with a control plasmid, showing that the immunoreactive material was derived from genetic material within VP2 and therefore probably represents hNGF. Because the EIUA is sensitive to dimerized hNGF, and because dimerization occurs only with mature NGF, these results show that the hNGF precursor encoded by the hNGF gene exon 4 fragment in VP2 is processed by the COS cells into mature hNGF, which is then secreted into the cultuyre medium.

Bioassay of Crude Medium

Secreted hNGF was also characterized by bioassay using PC12 cells. PC12 cells were grown in DMEM supplemented with 15% horse serum (KC Biologicals, Lexington, Ky.) and 10% fetal calf serum. For bioassay, PC12 cells were grown for two days in medium consisting of 2 parts PC12 cell medium and 1 part COS cell-conditioned medium. PC12 cells were then inspected for neurite outgrowth, and total RNA extracted by the guanidine thiocyanate and cesium chloride centrifugation method. When exposed to VP2-conditioned medium, but not when exposed to control medium, PC12 cells grew neurites, a response known to be elicited by NGF, although difficult to quantitate and sometimes occurring non-specifically.

A second and more specific response was also used as a bioassay for NGF activity. NGF is known to induce neuropeptide Y mRNA ("NPY mRNA") in PC12 cells over a 12 to 24 hour period. 10 µg of total RNA were assayed by Northern blot hybridization as described above for the NPY mRNA. The probe was a $^{32}$P-labeled cRNA prepared by in vitro transcription of a previously cloned cDNA template using SP6 RNA polymerase, as described in J. M. Allen et al., Mol. Brain Res., Vol. 3, pp. 39–43 (1987). Hybridization was carried out in 50% formamide and 1M NaCl at 65° C. The blot was washed in 0.3M NaCl at 65° C., and total RNA visualized by autoradiography. The blot was then digested for 15 min at 37° C. in 0.3M NaCl, 100 mM Tris, pH 7.5 containing 1 µg/ml RNAse A to remove nonspecifically bound probe, and autoradiography was repeated. NPY mRNA was induced in PC12 cells by medium conditioned by VP2 transfected COS cells, and not by control medium.

Fractionation of Crude Medium by Permeation Gel Chromatography

The secreted hNGF was physically characterized by column chromatography. 2 ml of medium conditioned for two days by VP2-transfected COS cells were fractionated on a 1×75 cm Sephadex G-75 column. The column was equilibria with 50 mM TRIS, pH 7.4, containing 100 mM NaCl, and medium eluted with the same buffer in 2 ml fractions. A mixture of molecular weight standards was fractionated in a separate run on the same column under identical conditions. The fractionations were carried out at 4° C. 50 µl aliquots of every other fraction were added to 50 µl of EIA sample buffer, and assayed for rhNGF by EIA. Molecular weight markers were identified by measuring the OD of 1 ml aliquots of each fraction at 280 nm. Immunoreactive material eluted from the column at an apparent molecular weight of 26–29 Kd, which is the molecular weight expected of a hNGF dimer. A second peak was observed at the expected molecular weight of the monomer.

Use

Human NGF produced according to the invention can be used where indicated for treatment of any of a variety of conditions of humans, such as, for example, Alzheimer's disease. The amount of NGF used will depend upon the type and severity of the condition being treated, the route of administration, and the specific activity of the NGF; these parameters can be determined by conventional means by one of ordinary skill in this field.

Human NGF according to the invention can be administered by any route appropriate for the condition being treated, and one skilled in the art will appreciate that the preferred route will vary according to the condition being treated.

The human NGF of the invention can be administered as the pure or substantially pure compound, it preferably will be presented as a pharmaceutical formulation or preparation, in which the hNGF is combined with a pharmaceutically acceptable carrier, and, optionally, with other therapeutic ingredients. Pharmaceutically acceptable carriers, well known to those skilled in the pharmacological art, are compatible with other ingredients of the formulation, and not deleterious to the patient. The pharmaceutical formulations conveniently are made available in unit dosage form and can be prepared by any of the methods well known in the pharmaceutical art. The formulations can be prepared for example by bringing the hNGF into uniform and intimate association with liquid carriers or finely divided solid carriers, or both, and then, if necessary, shaping the product into the desired formulation. Formulations suitable for parenteral administration conveniently comprise sterile aqueous solutions of the hNGF with solutions which preferably are isotonic with the blood of the patient. Such formulations can conveniently be prepared by dissolving solid hNGF in water to produce an aqueous solution, and sterilizing the solution.

OTHER EMBODIMENTS

Other embodiments are within the following claims. For example, the invention can be practiced using any of a variety of cell types, and preferably mammalian cell types, using appropriate expression vectors, as described for example in U.S. Pat. No. 4,740,461, hereby incorporated by reference, and as are well known in the art.

Expression vectors according to the invention can be constructed by methods well known to those skilled in the art Components of the vectors can be obtained from natural sources or synthesized by known procedures, as decribed for example in Kaufman et al., Jour. Mol. Biol., Vol. 159, pp. 601–21 (1982), and Kaufman, proc. Natl. Acad. Sci., Vol. 82, pp. 689–93 (1985). The expression vectors can also include inducible expression systems as are known in the art, as described for example in International Patent Application No. PCT/US87/01871.

The host cells for the expression vectors of the invention preferably are any of a number of established mammalian cell lines. Preferably the expression vector DNA will be stably integrated into the chromosomal DNA of the host cell, and preferably the integrated vector DNA will be subsequently amplified. Such integration and amplification can conveniently be carried out in Chinese hamster ovary ("CHO") cells using convention methods, and for these purpose CHO cells can be preferred as hosts.

Alternatively the expression vector DNA can include all or part of the bovine papilloma virus genome, as described in Lusky et al., Cell, Vol. 36, pp. 392-401 (1984), and such a vector can be carried as a stable episomal element in a cell line such C127 mouse cells.

Any of a variety of established cell lines, including transformed cell lines, can be suitable as hosts. Normal diploid cells, cell strains derived from in vitro culture of primary tissue, and primary explants, including relatively undifferentiated cells such as hematopoetic stem cells, can also be suitable. Thus, useful mammalian cell lines can include HeLa, melanoma cell lines such as Bowes cells, mouse L-929 cells, 3T3 cell lines derived from Swiss, Balb-c, or NIH mice, BHK or HaK hamster cell liens, and the like.

I claim:

1. A vector capable of replicating in a mammalian cell, said vector comprising a human prepro-NGF encoding DNA sequence consisting essentially of the coding region of exon 4 of the human NGF gene and regulator DNA operationally associated with and capable of effecting the expression of said human prepro-NGF encoding DNA sequence, said vector being capable of expressing biologically active recombinant human NGF in said mammalian cell.

2. A mammalian cell transfected with the expression vector of claim 1.

3. The mammalian cell of claim 2 wherein said cell is transiently transfected with said expression vector.

4. The mammalian cell of claim 3 wherein said cell is stably transfected with said expression vector.

5. Plasmid VP2.

6. A mammalian cell transfected with the plasmid of claim 5.

7. The cell of claim 6, said cell being a COS cell.

8. The cell of claim 6, said cell being a CHO cell.

9. A method for making recombinant human nerve growth factor, comprising transfecting a mammalian cell with the expression vector of claim 1, maintaining said mammalian cell in a culture medium, and isolating recombinant human nerve growth factor from said medium.

* * * * *